United States Patent
Krishnan et al.

(10) Patent No.: US 6,316,469 B1
(45) Date of Patent: Nov. 13, 2001

(54) USE OF SELECTIVE SEROTONIN REUPTAKE INHIBITORS FOR TREATMENT OF CHEST PAIN OF NON-CARDIAC ORIGIN AND GASTRO-ESOPHAGEAL REFLUX DISEASE

(75) Inventors: Krishnaswamy Ranga Krishnan, Chapel Hill; Christopher O'Connor, Durham; Indira Varia, Chapel Hill, all of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/516,961

(22) Filed: Mar. 1, 2000

(51) Int. Cl.[7] .................. A61K 31/445; A61K 31/34; A61K 31/15; A61K 31/135
(52) U.S. Cl. ................. 514/321; 514/469; 514/640; 514/649; 514/657
(58) Field of Search .................. 514/321, 469, 514/640, 649, 657

(56) References Cited

U.S. PATENT DOCUMENTS

| | | |
|---|---|---|
| 4,868,218 | 9/1989 | Buyske . |
| 5,016,652 | 5/1991 | Rose et al. . |
| 5,380,761 | 1/1995 | Szabo et al. . |

OTHER PUBLICATIONS

Mayou et al., "Management of Non–Cardiac Chest Pain: from Research to Clinical Practice," Heart, pp. 387–392 (1999).
Jolobe, "Comparative Study of Chest Pain Characteristics in Patients with Normal and Abnormal Coronary Angiograms," Heart, vol. 80, No. 2, p. 210 (Aug., 1998).
Cannon, "The Conundrum of Cardiovascular Syndrome X," Cardiiology in Review, vol. 6, No. 4, pp. 213–220, (1998).
Cox et al., "Low Dose Imipramine Improves Chest Pain but Not Quality of Life in Patients with Angina and Normal Coronary Angiograms," European Heart Journal, pp. 250–254 (1998).
Cannon, "How to Manage Chest Pain in Patients with Normal Coronary Angiograms," Cardiologia, vol. 42, No. 1, pp. 21–29 (1997).
Chambers, "Chest Pain: Heart, Body or Mind?," Journal of Psychosomatic Research, vol. 43, No. 2, pp. 161–165 (1997).
Cannon, "Does Coronary Endothelial Dysfunction Cause Myocardial Ischemia in the Absence of Obstructive Coronary Artery Disease?," Circulation, vol. 96, No. 10, pp. 3251–3254 (Nov. 18, 1997).
Holdright, "Chest Pain with Normal Coronary Arteries," British Journal of Hospital Medicine, vol. 56, No. 7, pp. 347–350 (1996).
Cannon, "Chest Pain and the Sensitive Heart," European Journal of Gastroenterology & Hepatology, vol. 7, No. 12, pp. 1166–1171 (1995).

Cannon, "The Sensitive Heart—A Syndrome of Abnormal Cardiac Pain Perception," JAMA, vol. 273, No. 11, pp. 883–887 (Mar. 15, 1995).
Cannon et al., "Imipramine in Patients with Chest Pain Despite Normal Coronary Angiograms," The New England Journal of Medicine, vol. 330, No. 20, pp. 1411–1417 (May 9, 1994).
Cannon,, "Chest Pain with Normal Coronary Angiograms," The New England Journal of Medicine, pp. 1706–1708 (Jun. 10, 1993).
Cannon et al., "Chest Pain as a Consequence of Abnormal Visceral Nociceptionn," Digestive Diseases and Sciences, vol. 38, No. 2, pp. 193–196 (Feb., 1993).
Potts et al., "Psychosocial Outcome and Use of Medical Resources in Patients with Chest Pain and Normal or Near–Normal Coronary Arteries: A Long–Term Follow–Up Study," Quaterly Journal of Medicine, vol. 86, pp. 583–593 (1993).
Quyyumi, et al., "Endothelial Dysfunction in Patientw with Chest Pain and Normal Coronary Arteries," Circulation, vol. 86, No. 6, pp. 1864–1871 (Dec., 1992).
Richter et al., "Chest Pain with Normal Coronary Arteries," Digestive Diseases and Sciences, vol. 35, No. 12, pp. 1441–1444 (Dec., 1990).
Richter et al., "Esophageal Chest Pain: Current Controversies in Pathogenesis, Diagnosis, and Therapy," Annals of Internal Medicine, vol. 110, No. 1, pp. 66–78 (Jan. 1, 1989).
Lantinga et al., "One–Year Psychosocial Follow–Up of Patients with Chest Pain and Angiographically Normal Coronary Arteries," The America Journal of Cardiology, vol. 62, pp. 209–213 (Aug. 1, 1988).
Cannon, "Causes of Chest Pain in Patients with Normal Coronary Angiograms: The Eye of the Beholder," The American Journal of Cardiology, vol. 62, pp. 306–308 (Aug. 1, 1988).
Katon et al., "Chest Pain: Relationship of Psychiatric Illness to Coronary Arteriographic Results," The American Journal of Medicine, vol. 84, No. 1, pp. 1–9 (Jan., 1988).
Papanicolaou et al., "Prognostic Implications of Angiographically Normal and Insignificantly Narrowed Coronary Arteries," American Journal of Cardiology, vol. 58, pp. 1181–1187 (Dec. 1, 1986).
Kemp et al., "Seven Year Survival of Patients with Normal or Near Normal Coronary Arteriograms: A CASS Registry Study," Journal of American College of Cardiology, vol. 7, No. 3, pp. 479–483 (Mar., 1986).
Cannon, "Can Measures of Coronary Dynamics Explain Chest Pain Without Coronary Artery Disease?", Mayo Clinic Proceedings, vol. 73, No. 12, pp. 1226–1228 (Dec., 1998).

(List continued on next page.)

*Primary Examiner*—William R. A. Jarvis

(57) ABSTRACT

Selective serotonin reuptake inhibitors useful in the treatment of non-cardiac chest pain or the treatment of symptoms of gastro-esophageal reflux disease.

12 Claims, 2 Drawing Sheets

OTHER PUBLICATIONS

Dart et al., "Chest Pain with Normal Coronary Arteries," The Lancet, p. 311 (Feb. 9, 1980).

Dart et al., "Angina' and Normal Coronary Arteriograms: A Follow–Up Study," European Heart Journal, vol. 1., pp. 97–100 (Jan., 1980).

Kemp et a., "The Anginal Syndrome Associated with Normal Coronary Arteriograms. Report of a Six Year Experience," The American Journal of Medicine, vol. 54, pp. 735–742 (Jun., 1973).

Proudfit et al., "Selective Cine Coronary Arteriography. Correlation with Clinical Findings in 1,000 Patients," Circulation, vol. 33, pp. 901–910 (Jun., 1966).

USE OF SELECTIVE SEROTONIN REUPTAKE INHIBITORS FOR TREATMENT OF CHEST PAIN OF NON-CARDIAC ORIGIN AND GASTRO-ESOPHAGEAL REFLUX DISEASE

TECHNICAL FIELD

The present invention relates in general to treatment of a medical condition. More particularly, the present invention relates to a new use of a selective serotonin reuptake inhibitor (which medicament is already known for use in treatment of depression) in the treatment of chest pain of non-cardiac origin. In an alternative embodiment, another new use of a selective serotonin reuptake inhibitor is in the treatment of symptoms of gastro-esophageal reflux disease.

Table of Abbreviations

| | |
|---|---|
| angio | angiogram |
| BDI | Beck Depression Inventory |
| BP | bodily pain |
| DSM-IV | Diagnostic and Statistical Manual for Mental Disorders, 4$^{th}$ Edition, published by the American Psychiatric Association |
| D | drug |
| GERD | gastro-esophageal reflux disease |
| GH | general health |
| kg | kilogram |
| LCI | lower confidence interval |
| L95 CI | 95% lower confidence interval |
| MH | mental health |
| mg | milligram |
| MAOI | monoamine oxidase inhibitor |
| neg | negative |
| N | number of persons in test sample |
| OLS | ordinary least squares |
| PF | physical functioning |
| P | placebo |
| RH | reported health |
| RE | role--emotional |
| RP | role--physical |
| SSRI | selective serotonin reuptake inhibitor |
| SF | Social Functioning |
| SF36 | Social Functioning Health Survey Manual |
| STD ERR | standard error |
| PROB | Student's t-test |
| UCI | upper confidence interval |
| U95 CI | 95% upper confidence interval |
| VAIS-PR | visual analogue inventory scale--pain response |
| wk | week |

BACKGROUND

Between 10–30% of patients with symptoms similar to angina and sufficient to justify cardiac catheterization are often found to have normal coronary angiograms. Since coronary artery disease (the typical organic cause of chest pain) is not the cause of the chest pain, management of chest pain patients with no apparent cardiac etiology is a major clinical problem.

Most of these patients continue to experience chest pain, often resulting in visits to the emergency room and occasionally even repeat cardiac catheterization. See, for instance, Papanicolaou et al., "Prognostic Implications of Angiographically Normal and Insignificantly Narrowed Coronary Arteries", Am. J. Cardiol., 58(13): 1181–1187 (Dec. 1, 1986); Proudfit et al., "Selective Cine Coronary Arteriography. Correlation with Clinical Findings in 1,000 Patients", Circulation, 33(6): 901–910 (June, 1966); Dart et al., "Angina' and Normal Coronary Arteriograms: A Follow-up Study", Eur. Heart J., 1(2): 97–100 (1980); Dart et al., "Chest Pain with Normal Coronary Arteries", Lancet, 1(8163): 311 (Feb. 9, 1980); Kemp et al., "The Anginal Syndrome Associated with Normal Coronary Arteriograms. Report of a Six Year Experience", Am. J. Med., 54(6): 735–742 (June, 1973); Kemp et al., "Seven Year Survival of Patients with Normal or Near Normal Coronary Arteriograms: A CASS Registry Study", J. Am. Coll. Cardiol. 7(3): 479–483 (March, 1986.); and Cannon, R. O. 3$^{rd}$, "The Conundrum of Cardiovascular Syndrome X", Cardiol. in Rev., 6(4): 213–220 (1998).

Thus, the condition of non-cardiac chest pain has considerable effects on quality of life and utilization of health care resources, resulting from a poor symptomatic, functional, and psychological outcome. Although most patients with non-cardiac chest pain are discharged after being reassured, they rarely feel reassured and often desire additional clinical evaluations. The basis of unexplained chest pain and the management of patients who have unexplained chest pain, despite a normal coronary angiogram and/or a normal stress test, is controversial. They continue to believe that they have significant disease which has been missed. See, for instance, Lantinga et al., "One-year Psychosocial Follow-up of Patients with Chest Pain and Angiographically Normal Coronary Arteries", American Journal of Cardiology, 62 (4): 209–213, (Aug. 1, 1988); Potts et al., "Psychosocial Outcome and Use of Medical Resources in Patients with Chest Pain and Normal or Near-normal Coronary Arteries: A Long-term Follow-up Study", Q. Journal of Medicine, 86 (9): 583–593 (1993); Mayou et al., "Management of Non-cardiac Pain: from Research to Clinical Practice", Heart, 81(4): 387–392 (1999); Cannon, R. O. 3$^{rd}$, "Can Measures of Coronary Dynamics Explain Chest Pain without Coronary Artery Disease?", Mayo Clinic Proceedings, 73 (12): 1226–1228 (December, 1998); Cannon, R. O. 3$^{rd}$; "Does Coronary Endothelial Dysfunction Cause Myocardial Ischemia in the Absence of Obstructive Coronary Artery Disease?", Circulation, 96(10): 3251–3254 (Nov. 18, 1997); Richter et al., "Chest Pain with Normal Coronary Arteries. Another Perspective", Digestive Diseases and Sciences, 35(12): 1441–1444 (December, 1990); Cannon, R. O. 3$^{rd}$; "How to Manage Chest Pain in Patients with Normal Coronary Angiograms", Cardiologia, 42 (1): 21–29, (January, 1997); and Cannon, R. O. 3$^{rd}$; "Chest Pain and the Sensitive Heart", Eur. J. of Gastroenterol. & Hegatol., 7(12): 1166–1171 (1995).

Estimates are that a person with chest pain that is non-cardiac (because the coronary angiogram was normal) spends about $3,500 a year to manage this pain. See, for instance, Richter et al., "Esophageal Chest Pain: Current Controversies in Pathogenesis, Diagnosis, and Therapy", Annals of Internal Med., 110(1): 66–78 (Jan. 1, 1989). Furthermore, although coronary artery disease is ruled out to be the cause of the chest pain (since the coronary angiogram was normal), other medical causes exist, which can be the cause of the chest pain.

For instance, other medical causes of non-cardiac chest pain may be organic. Examples of organic causes include Prinzmetal angina, microvascular angina and potentially esophageal, rheumatological and pulmonary diseases. See, for instance, Chambers, "Chest Pain: Heart, Body or Mind?", Journal of Psychosomatic Research, 43(2): 161–167 (1997); and Jolobe et al., "Comparative Study of Chest Pain Characteristics in Patients with Normal and Abnormal Coronary Angiograms", Heart, 80(2): 210 (1998). However, frequently no organic cause can be found.

Also, other medical causes of non-cardiac chest pain may be psychiatric. More particularly, psychiatric evaluation of these patients with non-cardiac chest pain has suggested that a significant proportion of them may meet the criteria for panic disorder. Depressive symptoms may also occur in these patients. Many other patients also have some symptoms of anxiety, though these patients do not meet clinical diagnostic criteria for panic disorder and/or other psychiatric disorders. See, for instance, Katon et al., "Chest Pain: Relationship of Psychiatric Illness to Coronary Arteriographic Results", *The American Journal of Medicine*, 84(1): 1–9 (January 1988); and Cannon, R. O. $3^{rd}$, et al, "Imipramine in Patients with Chest Pain Despite Normal Coronary Angiograms", *The New England Journal of Medicine*, 330 (20): 1411–1417 (May 19, 1994).

An early randomized, double-blind, placebo-controlled study that used a psychotropic drug to evaluate the treatment of chest pain, despite normal coronary angiograms, was reported by Cannon et al. in "Imipramine in Patients . . . " supra. In this study, 60 patients, some with and some without psychiatric disorders, underwent treatment in a double-blind protocol receiving clonidine 0.1 mg (twice a day), imipramine (50 mg nightly), or placebo (twice a day). (Clondine is an antihypertensive, and imipramine is a tricyclic antidepressant and a member of the dibenzazepine group.) Patients were treated initially with a single blind placebo, given twice a day, and pain ratings were evaluated using a simple scale based on a daily pain diary. The patients were then randomized to either drug or placebo. The reduction in the frequency of chest pain in the imipramine group was approximately 50% compared to the placebo group. This benefit was seen irrespective of either current or past psychiatric disease. The effect was noted within 3 weeks. Also noted was a reduction in right ventricle sensitivity to pain.

The benefit of imipramine in the treatment of non-cardiac chest pain has been recently confirmed. See, for instance, Cox et al., "Low Dose lmipramine Improves Chest Pain but not Quality of Life in Patients with Angina and Normal Coronary Angiograms", *Eur. Heart J.*, 19(2):250–254 (February, 1998).

In another study reported by Cannon, R. O. $3^{rd}$, in "Does Coronary Endothelial Dysfunction . . . " supra is a suggestion that microvascular dysfunction may cause myocardial ischemia during stress in a subset of patients, particularly those who have abnormal stress tests, even through they have normal coronary angiograms. Additional studies reported by Cannon, R. O. $3^{rd}$, and one study reported by Quyyumi et al. suggest patients with chest pain, normal coronary angiograms, and ischemic appearing exercise electrocardiograms may have exaggerated or abnormal cardiac pain perception. See, for instance, Cannon, R. O. $3^{rd}$, "The Sensitive Heart. A Syndrome of Abnormal Cardiac Pain Perception", *JAMA*, 273(11): 883–887 (Mar. 15, 1995); Cannon, R. O. $3^{rd}$, "Chest Pain with Normal Coronary Angiograms", *N. Engl. J. Med.*, 328(23): 1706–1708 (Jun. 10, 1993); Cannon, R. O. $_3^{rd}$, "Chest Pain as a Consequence of Abnormal Visceral Nociception", *Dig. Dis. and Sci.*, 38(2): 193–196 (February, 1993); Quyyumi et al., "Endothelial Dysfunction in Patients with Chest Pain and Normal Coronary Arteries", *Circulation*, 86(6): 1864–1871 (December, 1992); Holdright, "Chest Pain with Normal Coronary Arteries", *Br. J. Hosp. Med.*, 56(7): 347–350 (1996); and Cannon, R. O. $3^{rd}$, "Causes of Chest Pain in Patients with Normal Coronary Angiograms: The Eye of the Beholder", *The American Journal of Cardiology*, 62: 306–308 (Aug. 1, 1988).

A medicament beneficial in treating patients with non-cardiac chest pain is clearly still needed. Also, a medicament beneficial in ameliorating the symptoms of GERD in patients with GERD is clearly still needed. Surprisingly, the present inventors have found that SSRIs are of benefit to these patients.

STATEMENT AND OBJECTS OF INVENTION

Therefore, the present invention provides a method for treating a human having non-cardiac chest pain. The method comprises administering a selective serotonin reuptake inhibitor to the human's upper gastro-intestinal tract so as to introduce the selective serotonin reuptake inhibitor to the metabolism of the human, and periodically repeating the administration so as to administer a therapeutically effective amount of the selective serotonin reuptake inhibitor to the human's metabolism sufficient to provide an analgesic effect to the human.

Also, the present invention provides a method for treating a human having gastro-esophageal reflux disease and exhibiting symptoms of gastro-esophageal reflux disease. The method comprises administering a selective serotonin reuptake inhibitor to the human's upper gastrointestinal tract so as to introduce the selective serotonin reuptake inhibitor to the metabolism of the human, and periodically repeating the administration so as to administer a therapeutically effective amount of the selective serotonin reuptake inhibitor to the human's metabolism sufficient to provide amelioration of the symptoms of gastro-esophageal reflux disease.

Hence, it is an object of the invention to provide an analgesic effect and thus to alleviate chest pain in persons for whom tests for an organic cause for the chest pain are negative and/or tests for a psychiatric cause for the chest pain are negative. It is an advantage of the invention that a non-cardiac chest pain patient so treated does not spend a great deal of money in repeat visits to the doctor in an attempt to find significant disease that the person mistakenly believes has been missed.

Additionally, it is another object of the invention that a GERD patient so treated will have the GERD symptoms alleviated.

Some of the objects of the invention having been stated above, other objects will become evident as the description proceeds when taken in connection with the accompanying Figures and Laboratory Example as best described below.

DETAILED DESCRIPTION OF THE INVENTION

Figure 1:
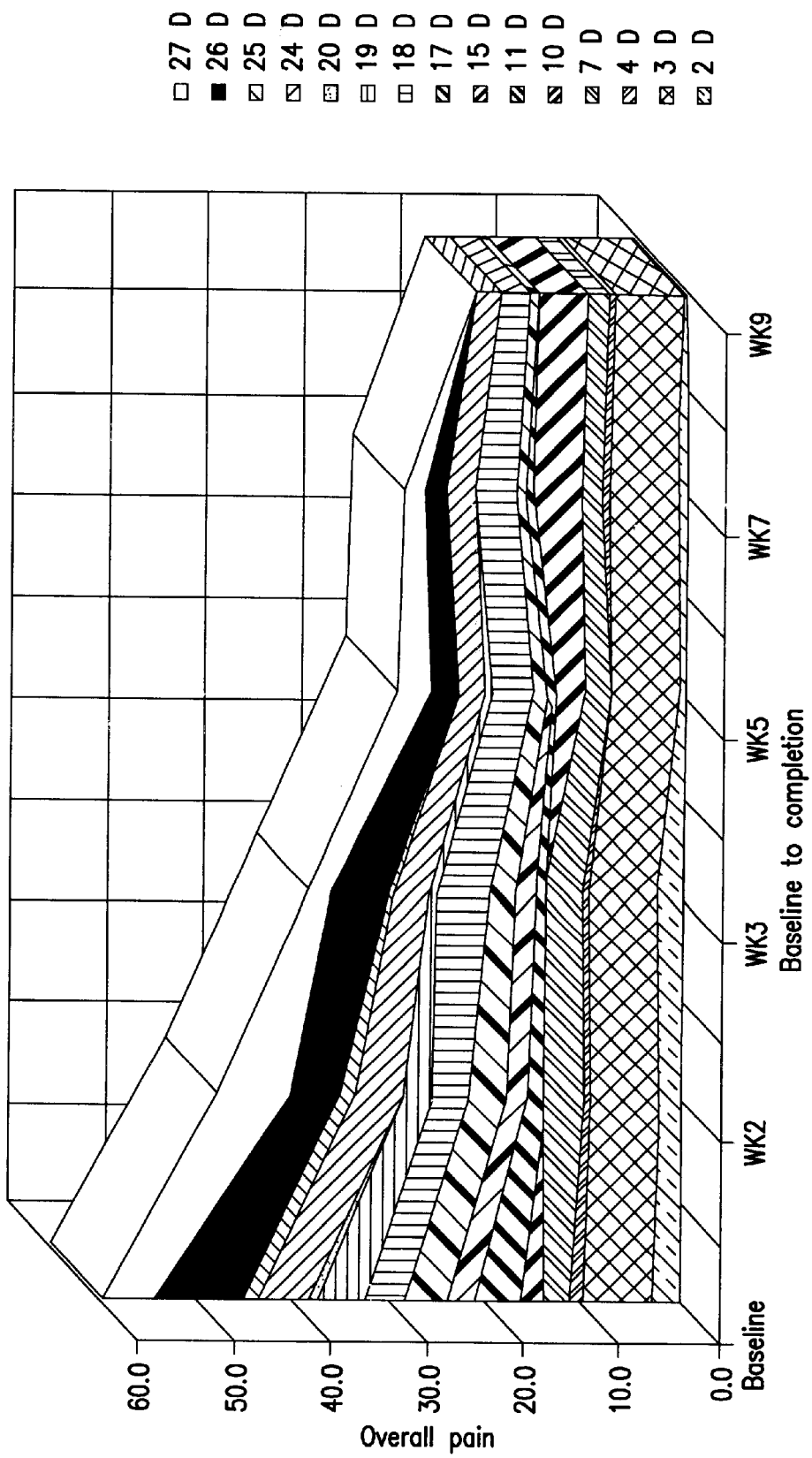
FIG. 1 is a graph showing the time course of chest pain reduction in test subjects receiving the drug sertraline. The column on the far right with various numerals, each followed by the letter "ED" for drug, reflects the patient number for each of the 15 patients on the drug.

Any selective serotonin reuptake inhibitor may be employed in the present invention for the treatment of non-cardiac chest pain, and/or for the treatment of GERD symptoms.

As is well known, the symptoms of GERD are a burning pain in the chest and an acid taste in the mouth. Drugs known to be useful for curing GERD are those that inhibit gastric acid secretion by competitive, reversible inhibition of the action of histamine at the histamine $H_2$ receptors including receptors on the gastric cells, such as ranitidine HCl (sold as a syrup, a tablet, and an injection by Glaxo Wellcome, Inc. under the trademark ZANTAC®) and cimetine HCl (sold as a liquid, a tablet, and an injection by SmithKline Beecham Pharmaceuticals under the trademark TAGAMET®), and those that inhibit gastric acid secretion by specific inhibition of the $H^+/K^+$ ATPase enzyme system at the secretory surface of the gastric parietal cell (and not by $H_2$ histamine antagonistic properties), such as omeprazole (sold as a delayed-release capsule by Merck & Co., Inc. under the trademark PRILOSEC®).

A suitable SSRl useful in the present invention includes, but is not limited to, sertraline (registered trademark ZOLOFT®—marketed by Pfizer), fluoxetine (registered trademark PROZAC®—marketed by Eli Lilly), paroxetine (trade name PAXiL™—marketed by Smith Kline Beecham), fluvoxamine (registered trademark LUVOX®—marketed by Solvay Pharmaceuticals), and/or citalopram (registered trademark CELEXA®—marketed by Forest). Each of citalopram and fluoxetine exists as a racemic mixture. Thus, not only are racemic citalopram and/or racemic fluoxetine useful, but also useful are levo citalopram, dextro citalopram, levo fluoxetine, and/or dextro fluoxetine.

A suitable amount for dosing ranges from about 25 to about 250 mg per day (about 0.25 to about 2.50 mg per kg of body weight), and more preferably from about 50 to about 200 mg (about 0.50 to about 2.00 mg per kg of body weight) per day. Dosing may be continued indefinitely and should be continued for at least about 1 to about 10 weeks, more preferably about 2 to about 9 weeks.

Administration of the SSRl may be oral, such as a tablet, powder, capsule, or solution, which may be orally administered by being swallowed. In addition to oral administration, contemplated also is that administration of the SSRl may be transdermal (such as with a skin patch). A good discussion of transdermal administration can be seen in U.S. Pat. No. 5,016,652 issued May 21, 1991 to Rose and Jarvik, U.S. Pat. No. 5,380,761 issued Jan. 10, 1995 to Szabo et al., and U.S. Pat. No. 4,868,218 issued Sep. 19, 1989 to Buyske.

For treatment of non-cardiac chest pain, the SSRl may be administered free of administration of medicaments such as aspirin, acetaminophen, naproxen sodium, celecoxib, indomathicin, and the like, that are known analgesic medicaments for the treatment of pain.

For treatment of GERD, the SSRl may be administered in conjunction with a medicament, such as omeprazole, ranitidine HCl, and the like, known for the treatment, including the cure, of GERD.

LABORATORY EXAMPLES

The study was a single site, double-blind, placebo-controlled study of the efficacy, tolerability, and safety of sertraline (an SSRl) in the treatment of non-cardiac chest pain in 30 patients or the treatment of GERD symptoms in 5 of those 30 patients who otherwise had at least one of a normal coronary angiogram and/or a normal stress test. Sertraline was ZOLOFT® supplied by Pfizer.

Patients were recruited through referrals from the Cardiology Service of Duke University, Durham, N.C., United States of America. The study was approved by the Medical Center Institutional Review Board of Duke University and conformed to all ethical guidelines of the Declaration of Helsinki.

Prospective patients were screened to rule out those who met exclusionary criteria, as discussed below. Then, the risks and the benefits of participation in the study were explained to each patient, after which, written informed consent was obtained and documented from each patient.

For those patients who gave informed consent, a single-blind placebo washout period (once a day dose for at least 7 days before the baseline visit) was conducted. Next, patients meeting entry criteria after the washout were subjected to baseline evaluations, and then randomization to active treatment with either sertraline or placebo for 8 weeks double-blind treatment. At the time of the baseline visit, a second screening was performed, as well as all other evaluations indicated below. Also, those patients who were included in the study agreed to abstain from alcohol and to adhere to protocol requirements.

Individual randomization was carried out by the investigational pharmacy using a computer generated schedule. To establish randomization, baseline measures of depression (BDl), pain (VAIS-PR: self-administered rating of pain on a scale of 1 to 10), SF36 values, age, and race were averaged and tested for differences between drug and placebo conditions. The drug and the placebo were identically packaged in capsule form, and patients were told to swallow the capsule with tap water. The code was broken only after the study was completed and the data cleaned. Investigators remained blind throughout the study, and analysis was conducted using a statistician who had no patient contact.

Patients rated their pain daily in the morning, reflecting the last 24 hours, on the VAIS-PR scale. These measures were collected at baseline and at weeks 2, 3, 5, 7, & 8. The BDl and SF36 were obtained at baseline and final visits. At baseline and at weeks 2, 3, 5, 7, & 8, adverse events were evaluated and vital signs taken. Patients discontinuing therapy prior to week 8 were evaluated for safety and efficacy at the time of their final visit.

Patients, 14 males and 16 females, ages 18–85, who were able to swallow oral medication and who were suffering from non-cardiac chest pain were recruited from the Cardiology Service of Duke University and evaluated for inclusion in the study. The classification of patients by race and gender was as designated in Table 1 below.

TABLE 1

CLASSIFICATION OF PATIENTS ACCORDING TO RACE AND GENDER

| Sertraline | | | Placebo | | |
| --- | --- | --- | --- | --- | --- |
| Number | Race | Gender | Number | Race | Gender |
| 4 | Black | Female | 1 | Black | Female |
| 1 | Arabic | Male | 2 | Black | Male |
| 5 | White | Female | 1 | Hispanic | Male |
| 5 | White | Male | 6 | White | Female |
| | | | 5 | White | Male |

Patients were designated as exhibiting non-cardiac chest pain after receiving at least one of a normal stress test and/or a normal coronary angiogram, classified as follows in Table 2 below.

TABLE 2

CLASSIFICATION OF PATIENTS ACCORDING TO CARDIAC WORK-UP

|  | Sertraline | Placebo | Total |
|---|---|---|---|
| Normal angio/normal stress test | 3 | 4 | 7 |
| Normal angio/no stress test | 2 | 0 | 2 |
| No angio/normal stress test | 10 | 11 | 21 |
| TOTALS | 15 | 15 | 30 |

On the other hand, patients were excluded from participation if they met the DSM-IV criteria for (1) major depression, (2) panic disorder, (3) drug abuse, (4) alcohol abuse, (5) drug dependence, or (6) alcohol dependence.

Also excluded were patients with various active or clinically significant conditions possibly affecting absorption, distribution, or metabolism of the study drug, e.g., (1) sensitivity to sertraline itself, (2) inflammatory bowel disease, (3) gastric ulcers, (4) duodenal ulcers, or (5) lactose intolerance.

Additionally, patients were ineligible if they had received treatment with (1) a depot (i.e., long acting) neuroleptic drug (i.e., haloperidol decanoate, proxilin decanoate, and the like) within 6 months of entering the study, (2) another antidepressant (within a period of less than 5 times the half-life of the drug concerned) before the start of the double-blind medication, (3) fluoxetine within 5 weeks of beginning the double-blind medication, or (4) a MAOI within the 3 weeks prior to the first administration of the double-blind medication. Of note, patients who became study participants were instructed not to take any MAOIs for 2 weeks after completing the study.

Furthermore, patients who required treatment with reserpine, methyidopa, guanethidine, clonidine, or who might, during the course of the study, have required local anesthetics, general anesthetics, or drugs known to interact with sertraline were excluded.

Lastly, patients who were taking anti-depressants, other psychotropic medications, or medications significantly effecting pain at the time of screening were also excluded.

These exclusions virtually eliminated the possibility that improvement was related to change in psychiatric symptoms and/or the possibility that the pain was from an organic cause.

A total of 34 patients were screened, of whom 30 enrolled in the single blind 7-day placebo washout. Of the 30 enrolled patients, 5 patients withdrew early due to non-compliance or scheduling conflicts—1 that had been assigned to the sertraline group and 4 that had been assigned to the placebo group.

Doses started at 50 mg/day and were adjusted to a maximum of 200 mg/day. Dosage was adjusted by the investigator based on patients' clinical responses.

A repeated measure analysis over 8 weeks for a sample size of 30 yielded a power of 0.09 at a 0.05 designated, approximate significance level for evaluating the statistical power of the sample (using the same kind of statistical analysis as in the above-noted imipramine studies). Comparison between the sertraline group and the placebo group with response defined in each group as a greater than 50% reduction of pain from baseline to week 8 yielded a power of 0.7400. Alternatively, responders classified by a VAIS-PR score of <1 endpoint yielded a power of 0.7307. Data from daily pain diaries (VAIS-PR) were averaged by week for analysis. Continuous measures meeting assumptions of normality were tested using student's t-test. Non-parametric Wilcoxon rank sum tests were used when conditions of normality did not hold. Categorical covariates were analyzed using chi square procedures.

Preliminary analyses of pain were tested in a series of bivariate comparisons of pain-by-drug condition using non-parametric Wilcoxon procedures. Outcomes were subsequently modeled using multivariable mixed model regression procedures. Such procedures, recognizing the correlated nature of repeated measures, directly model the covariance structure of outcome measures. Covariance structure was determined through comparisons of −2 log likelihood statistics derived from competing models. In the initial model, pain scores were regressed on main effect proxy variables representing time, drug condition, and the interaction between time and drug. Covariates were subsequently tested using this same basic model, entering all putative covariates both simultaneously and individually (due to concerns over collinearity).

Pain scores were also coded as a binary outcome with a weekly average score above 1 denoting presence of pain. Pain scores were also modeled over time using mixed model logistic regression. SF36 sub-scales and BDI scores were measured at the beginning and end-of-study time points. These scales were modeled as change in scores using student's t-test when distributional assumptions allowed and by non-parametric Wilcoxon procedures when tests of normality failed. All OLS models employed residual analyses when assumptions of normality were satisfied.

RESULTS

Tests of randomization between drug and placebo conditions at baseline were all negative with the exception of the SF36 sub-scale for role-emotional as summarized below in Table 3.

TABLE 3

BASELINE ANALYSES BY DRUG CONDITION

|  | PLACEBO (N = 15) | | SERTRALINE (N = 15) | |
|---|---|---|---|---|
|  | MEAN | STD ERR | MEAN | STD ERR |
| MALE | 0.53 | 0.13 | 0.40 | 0.13 |
| FEMALE | 0.47 | | 0.60 | |
| WHITE | 0.73 | 0.12 | 0.67 | 0.13 |
| BLACK | 0.20 | | 0.27 | |
| HISPANIC | 0.07 | | | |
| ARABIC | | | 0.07 | |
| SF36 GH | 62.13 | 5.25 | 64.60 | 5.68 |
| SF36 BP | 53.80 | 4.07 | 51.71 | 4.19 |
| SF36 HT | 48.33 | 5.70 | 56.67 | 5.70 |
| SF36 MH | 59.73 | 6.74 | 70.40 | 4.84 |
| SF36 PF | 66.00 | 6.80 | 71.00 | 6.44 |
| SF36 RE | 48.89 | 11.21 | 88.89 | **9.01 |
| SF36 RP | 51.67 | 11.30 | 63.33 | 10.87 |
| SF36 SF | 61.67 | 8.04 | 80.00 | 5.15 |
| SF36 VT | 43.00 | 5.93 | 55.00 | 4.68 |
| BDI | 9.87 | 1.64 | 9.20 | 1.87 |
| PAIN | 3.50 | 0.56 | 3.94 | 0.56 |

**$p <= 0.013$; WILCOXON CHI SQUARE

No other differences in outcome measures or covariates approached significance, indicating successful randomization, as summarized below in Table 4.

TABLE 4

REGRESSION ANALYSES OF WEEKLY PAIN SCORES RE NON-CARDIAC CHEST PAIN

|  | BETA | STD ERR | PROB | 95% LCI | 95% UCI |
|---|---|---|---|---|---|
| TIME | −0.05 | 0.07 | 0.45 | −0.19 | 0.08 |
| DRUG | 0.33 | 0.82 | 0.70 | −0.50 | 1.94 |
| TIME × DRUG | −0.21 | 0.10 | 0.03 | −0.40 | −0.02 |

Bivariate tests of differences in pain scores between experimental conditions by week were significant at week 8. See, Table 4 above.

There was an average 66% reduction of pain in the sertraline group compared to an average 8% reduction of pain in the controls who took the placebo ($p=0.045$). Thus, a marked decrease in pain scores over time was occurring among respondents receiving sertraline. See, FIG. 1. The fact that differences at the earlier time points failed to reach significance probably reflects power limitations of the small sample size used in this study.

Figure 2:
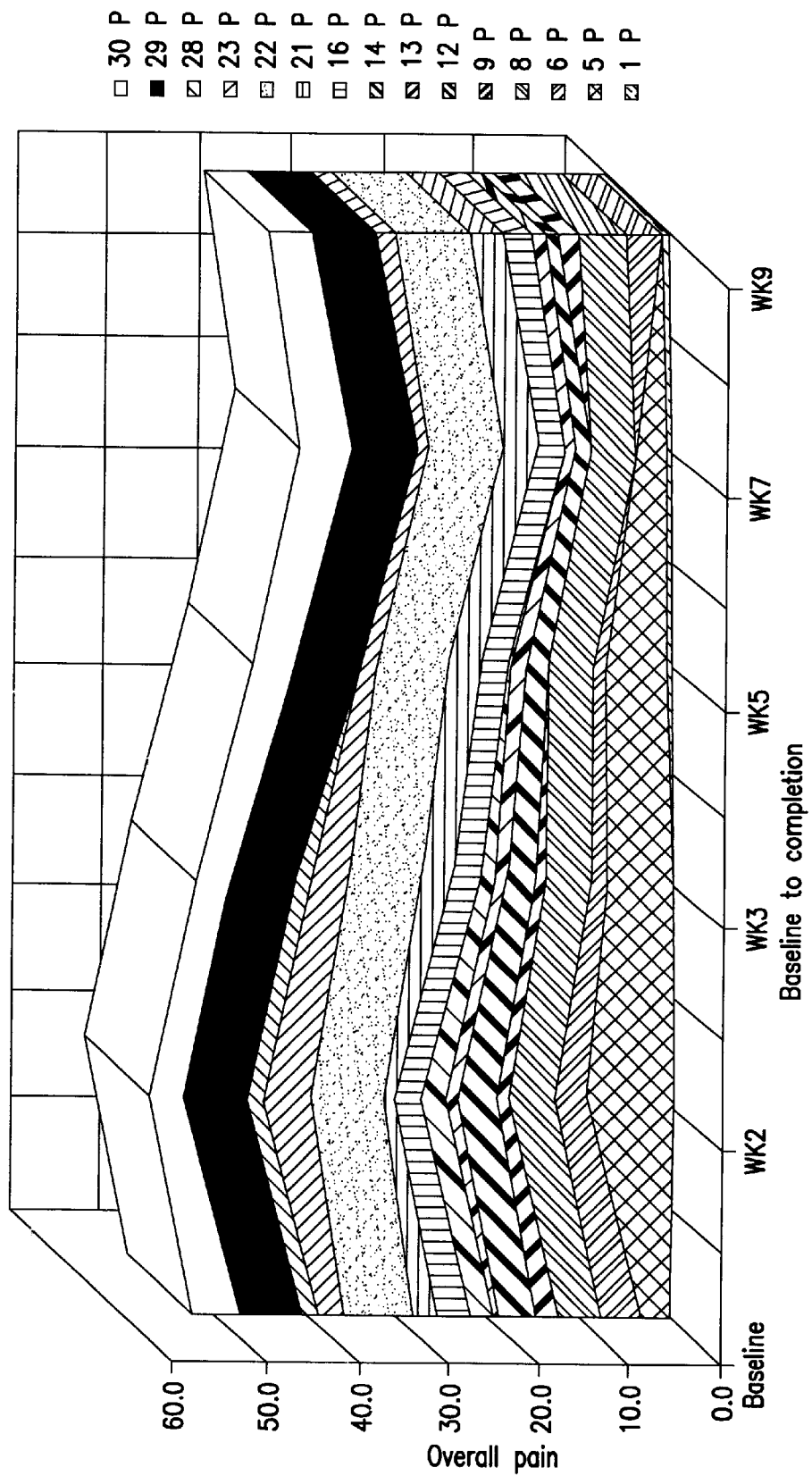
FIG. 2 is a graph showing the time course of chest pain reduction in test subjects receiving the placebo. The column on the far right with various numerals, each followed by the letter "P" for placebo, reflects the patient number for each of the 15 patients on the placebo.

In remodeling the same data using multivariable mixed model regression procedures, the coefficient associated with the interaction term between time and the experimental drug condition was significantly different at week 0. In other words, pain scores among respondents receiving sertraline decreased by approximately 0.20 units for each additional study week. The results are summarized below in Table 5. See also, FIGS. 1 and 2.

TABLE 5

BASELINE, END-OF-STUDY, AND CHANGE SCORES FOR SELECTED OUTCOMES BY DRUG CONDITION RE NON-CARDIAC CHEST PAIN

|  | WEEK 0 | WEEK 8 | DELTA |
|---|---|---|---|
| PLACEBO (N = 15) | | | |
| PAIN | 3.50 | 2.96 | −0.54 |
| BDI | 9.87 | 7.80 | −2.07 |
| SF36 BP | 53.80 | 58.47 | 4.67 |
| SF36 GH | 62.13 | 57.33 | 4.80 |
| SF36 HT | 48.33 | 43.33 | −5.00 |
| SF36 MH | 59.73 | 66.67 | 6.93 |
| SF36 PF | 66.00 | 65.00 | −1.00 |
| SF36 RE | 48.89 | 64.44 | 15.56 |
| SF36 RP | 51.67 | 56.67 | 5.00 |
| SF36 SF | 61.67 | 69.17 | 7.50 |
| SF36 VT | 43.00 | 46.33 | 3.33 |
| SERTRALINE (N = 15) | | | |
| PAIN | 3.94 | 1.47 | −2.47 |
| BDI | 9.20 | 6.07 | −3.13 |
| SF36 BP | 51.71 | 56.07 | 6.79 |
| SF36 GH | 64.60 | 66.93 | 2.33 |
| SF36 HT | 56.67 | 66.67 | 10.00 |
| SF36 MH | 70.40 | 76.27 | 5.87 |
| SF36 PF | 71.00 | 76.00 | 5.00 |
| SF36 RE | 88.89 | 77.78 | −11.00 |
| SF36 RP | 63.33 | 85.00 | 21.67 |
| SF36 SF | 80.00 | 85.83 | 5.83 |
| SF36 VT | 55.00 | 54.00 | −1.00 |

|  | DIFFERENCE (DRUG MINUS PLACEBO) | L95 CI | U95 CI | PROB |
|---|---|---|---|---|
| PAIN | −1.92 | −3.49 | −0.36 | 0.02 |
| BDI | −1.07 | −2.89 | 0.75 | 0.58 |
| SF36 BP | 2.12 | −12.57 | 16.81 | 0.77 |
| SF36 GH | 7.13 | 1.31 | 12.96 | 0.02 |
| SF36 HT | 15.00 | −4.35 | 34.35 | 0.12 |
| SF36 MH | −1.07 | −13.04 | 10.91 | 0.86 |
| SF36 PF | 6.00 | −6.17 | 18.17 | 0.32 |
| SF36 RE | −26.67 | −57.58 | 4.25 | 0.09 |
| SF36 RP | 16.67 | −12.92 | 46.26 | 0.26 |
| SF36 SF | −1.67 | −15.95 | 12.61 | 0.81 |
| SF36 VT | −4.33 | −18.18 | 9.51 | 0.53 |

Similarly, bivariate tests of beginning-of-study to end-of-study differences in BDI scores and SF36 subscales were all non-significant with the exception of the SF36 subscale for general health. The latter was significantly associated with drug condition, as can be seen from the above Table 3. Inspection of the data indicated that this was mediated by a decrease in scores at the end-of-study time point for the controls who took the placebo.

The finding of a good response in pain reduction with an SSRI for patients with non-cardiac chest pain suggests that inhibition of reuptake of serotonin may be critical in treating chest pain of non-cardiac origin.

Of the 30 patients noted in Table 2 above, 5 patients had GERD, classified as follows in Table 6 below.

TABLE 6

CLASSIFICATION OF GERD PATIENTS

|  | Sertraline | Placebo |
|---|---|---|
| Normal angio/normal stress test |  | 3 |
| No angio/normal stress test | 2 |  |

Those 2 who had taken sertraline reported a 61% decrease in GERD symptoms as compared to a 25% decrease in GERD symptoms reported by those 3 who had taken the placebo.

It will be understood that various details of the invention may be changed without departing from the scope of the invention. Furthermore, the foregoing description is for the purpose of illustration only, and not for the purpose of limitation'the invention being defined by the claims.

What is claimed is:

1. A method for treating a human having non-cardiac chest pain comprising:
    (a) administering a selective serotonin reuptake inhibitor to the human's upper gastro-intestinal tract so as to introduce the selective serotonin reuptake inhibitor to the metabolism of the human; and
    (b) periodically repeating (a), so as to administer a therapeutically effective amount of the selective serotonin reuptake inhibitor to the human's metabolism sufficient to provide an analgesic effect to the human.

2. The method of claim 1, wherein the selective serotonin reuptake inhibitor is free of having other medicaments administered therewith for treatment of pain.

3. The method of claim 1, wherein steps (a) and (b) are accomplished at least once per day.

4. The method of claim 1, wherein the amount of the selective serotonin reuptake inhibitor administered is sufficient to provide at least about 0.25 mg per kg of body weight per day.

5. The method of claim 1, wherein the selective serotonin reuptake inhibitor is selected from group consisting of sertraline, racemic fluoxetine, levo fluoxetine, dextro fluoxetine, paroxetine, fluvoxamine, racemic citalopram, levo citalopram, dextro citalopram, and combinations thereof.

6. The method of claim 1, wherein tests on the human for an organic cause of the chest pain are negative.

7. A method for treating a human having gastro-esophageal reflux disease and exhibiting symptoms of gastro-esophageal reflux disease comprising:
   a) administering a selective serotonin reuptake inhibitor to the human's upper gastrointestinal tract so as to introduce the selective serotonin reuptake inhibitor to the metabolism of the human; and
   (b) periodically repeating (a), so as to administer a therapeutically effective amount of the selective serotonin reuptake inhibitor to the human's metabolism sufficient to provide amelioration of the symptoms of gastro-esophageal reflux disease.

8. The method of claim 7, wherein the selective serotonin reuptake inhibitor is administered in conjunction with other medicaments for the treatment of gastro-esophageal reflux disease.

9. The method of claim 8, wherein the medicaments for the treatment of gastro-esophageal reflux disease are selected from the group consisting of omeprazole, ranitidine HCl, and combinations thereof.

10. The method of claim 7, wherein steps (a) and (b) are accomplished at least once per day.

11. The method of claim 7, wherein the amount of the selective serotonin reuptake inhibitor administered is sufficient to provide at least about 0.25 mg per kg of body weight per day.

12. The method of claim 7, wherein the selective serotonin reuptake inhibitor is selected from group consisting of sertraline, racemic fluoxetine, levo fluoxetine, dextro fluoxetine, paroxetine, fluvoxamine, racemic citalopram, levo citalopram, dextro citalopram, and combinations thereof.

* * * * *